US011707216B2

(12) United States Patent
Friant

(10) Patent No.: US 11,707,216 B2
(45) Date of Patent: Jul. 25, 2023

(54) RECOMMENDATIONS BASED ON BIOMETRIC FEEDBACK FROM WEARABLE DEVICE

(71) Applicant: Comcast Cable Communications, LLC, Philadelphia, PA (US)

(72) Inventor: Sarah Friant, Philadelphia, PA (US)

(73) Assignee: Comcast Cable Communications, LLC, Philadelphia, PA (US)

( * ) Notice: Subject to any disclaimer, the term of this patent is extended or adjusted under 35 U.S.C. 154(b) by 866 days.

(21) Appl. No.: 15/215,677

(22) Filed: Jul. 21, 2016

(65) Prior Publication Data

US 2018/0020963 A1 Jan. 25, 2018

(51) Int. Cl.
| | |
|---|---|
| *G06Q 30/00* | (2023.01) |
| *A61B 5/16* | (2006.01) |
| *G06Q 30/0251* | (2023.01) |
| *A61B 5/00* | (2006.01) |
| *H04L 67/306* | (2022.01) |
| *H04L 67/53* | (2022.01) |
| *H04L 67/50* | (2022.01) |

(52) U.S. Cl.
CPC ............ *A61B 5/165* (2013.01); *A61B 5/6801* (2013.01); *G06Q 30/0269* (2013.01); *H04L 67/306* (2013.01); *H04L 67/53* (2022.05); *H04L 67/535* (2022.05)

(58) Field of Classification Search
CPC ........................................ G06Q 30/02–0277
USPC .......................................................... 705/14
See application file for complete search history.

(56) References Cited

U.S. PATENT DOCUMENTS

| | | | |
|---|---|---|---|
| 6,904,408 B1 * | 6/2005 | McCarthy ............ | A61B 5/6815 705/2 |
| 8,401,248 B1 * | 3/2013 | Moon ................ | G06K 9/00597 382/118 |
| 9,105,047 B1 * | 8/2015 | Curran ............... | G06Q 30/0255 |
| 9,569,986 B2 * | 2/2017 | Levine .................. | A61B 3/112 |
| 9,712,587 B1 * | 7/2017 | Alfishawi .......... | G06Q 30/0269 |

(Continued)

FOREIGN PATENT DOCUMENTS

| | | | | |
|---|---|---|---|---|
| CA | 2662632 A1 * | 3/2008 | ............... | A61B 5/16 |
| KR | 20160095464 A * | 2/2015 | | |
| WO | WO-2015135066 A1 * | 9/2015 | ............. | G06F 17/00 |

OTHER PUBLICATIONS

"What will it take to find a human pheromone?" Katsnelson, Alla. Chemical and Engineering News, vol. 94 Issue 46 | pp. 23-25, Nov. 21, 2016. Retrieved from the Internet on Mar. 2, 2020: <https://cen.acs.org/articles/94/i46/take-find-human-pheromone.html>.*

(Continued)

*Primary Examiner* — Michael Bekerman
(74) *Attorney, Agent, or Firm* — Banner & Witcoff, Ltd.

(57) ABSTRACT

Methods and architecture for using sensor data to offer content, such as purchase or viewing suggestions, to a viewer, are disclosed. Wearable or other external sensor devices may monitor a viewer while the viewer consumes a first media element. The sensor data may then be used to determine an emotional response of the viewer to the media element or to entities found within that element, such as actors, scenes, brands, or objects. Emotional response data for a user may be stored, and may be used either immediately or at a later time to deliver content or make content or purchase suggestions to the viewer.

25 Claims, 7 Drawing Sheets

(56) References Cited

U.S. PATENT DOCUMENTS

| | | | |
|---|---|---|---|
| 9,936,250 B2* | 4/2018 | Marci | A61B 5/165 |
| 2009/0079547 A1* | 3/2009 | Oksanen | G06Q 30/02 |
| | | | 340/10.3 |
| 2009/0112810 A1* | 4/2009 | Jung | G06F 16/9032 |
| 2009/0113298 A1* | 4/2009 | Jung | G06F 3/011 |
| | | | 715/700 |
| 2011/0119124 A1* | 5/2011 | Pradeep | G06Q 30/02 |
| | | | 705/14.42 |
| 2011/0161163 A1* | 6/2011 | Carlson | G06Q 30/02 |
| | | | 705/14.44 |
| 2012/0324492 A1* | 12/2012 | Treadwell, III | H04H 60/45 |
| | | | 725/10 |
| 2013/0080260 A1* | 3/2013 | French | H04H 60/33 |
| | | | 705/14.66 |
| 2013/0110617 A1* | 5/2013 | Phan | H04W 4/21 |
| | | | 705/14.43 |
| 2013/0166372 A1* | 6/2013 | Abraham | G06Q 30/0269 |
| | | | 705/14.42 |
| 2013/0280682 A1* | 10/2013 | Levine | A61B 5/486 |
| | | | 434/236 |
| 2014/0067828 A1* | 3/2014 | Archibong | G06F 17/30277 |
| | | | 707/748 |
| 2014/0129347 A1* | 5/2014 | Pradeep | G06Q 30/0269 |
| | | | 705/14.66 |
| 2014/0223462 A1* | 8/2014 | Aimone | A61B 5/0476 |
| | | | 725/10 |
| 2014/0323817 A1* | 10/2014 | el Kaliouby | G16H 20/40 |
| | | | 600/300 |
| 2015/0058123 A1* | 2/2015 | Lenahan | G06Q 30/0255 |
| | | | 705/14.58 |
| 2015/0070516 A1* | 3/2015 | Shoemake | H04N 21/42203 |
| | | | 348/207.11 |
| 2015/0199730 A1* | 7/2015 | Soon-Shiong | G06Q 30/0269 |
| | | | 705/14.66 |
| 2015/0348162 A1* | 12/2015 | Morris | G06Q 30/0631 |
| | | | 705/26.7 |
| 2016/0063318 A1* | 3/2016 | Cheatham, III | G06K 9/00335 |
| | | | 348/143 |
| 2016/0317074 A1* | 11/2016 | Kawai | G16H 50/30 |
| 2016/0350801 A1* | 12/2016 | Vincent | G06Q 30/0251 |
| 2017/0068994 A1* | 3/2017 | Slomkowski | G06Q 30/0269 |
| 2017/0228774 A1* | 8/2017 | Sallas | G06F 16/9535 |
| 2017/0238859 A1* | 8/2017 | Sadowsky | A61B 5/6801 |
| 2017/0257410 A1* | 9/2017 | Gattis | H04N 21/8455 |
| 2017/0295402 A1* | 10/2017 | Courouge | G06K 9/00744 |
| 2017/0374414 A1* | 12/2017 | Knox | H04N 21/44218 |
| 2018/0303397 A1* | 10/2018 | Krupat | A61B 5/0077 |
| 2019/0041984 A1* | 2/2019 | Lee | G06F 3/013 |

OTHER PUBLICATIONS

Ohme, Ratal, Michal Matukin, and Beata Pacula-Lesniak. "Biometric Measures for Interactive Advertising Research." Journal of Interactive Advertising 11.2 (2011): 60-72. (Year: 2011).*

Consoli, Domenico. "A new concept of marketing: The emotional marketing." BRAND. Broad Research in Accounting, Negotiation, and Distribution 1.1 (2010): 52-59. (Year: 2010).*

Schreuder, Eliane, et al. "Emotional responses to multisensory environmental stimuli: A conceptual framework and literature review." Sage Open 6.1 (2016): 2158244016630591. (Year: 2016).*

* cited by examiner

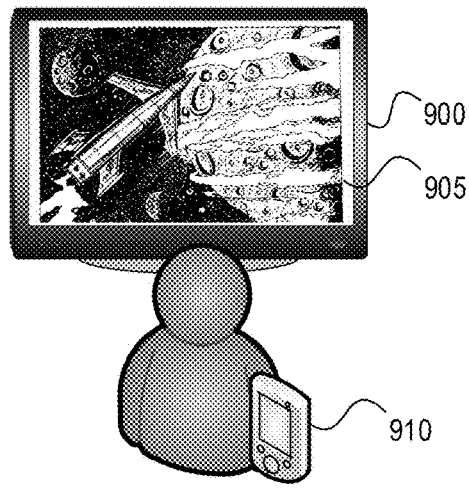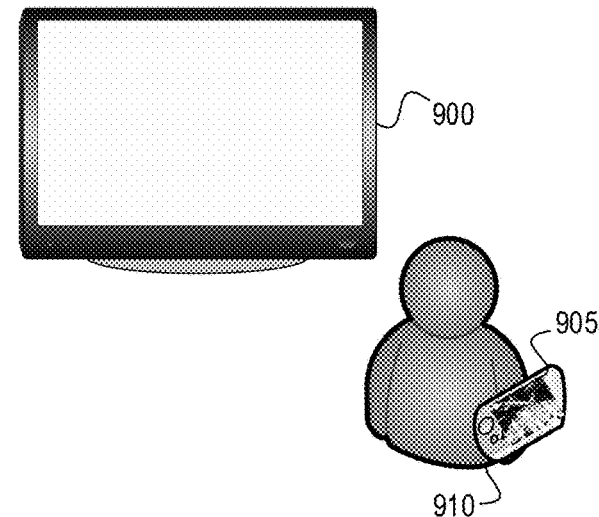
Fig. 9a
Fig. 9b
Fig. 10

RECOMMENDATIONS BASED ON BIOMETRIC FEEDBACK FROM WEARABLE DEVICE

FIELD

Aspects described herein generally relate to targeting media and purchases to interested consumers. More specifically, aspects provide for detecting a variety of biological or behavioral parameters while a viewer consumes media and using that information to select additional media which may be desired by the viewer.

BACKGROUND

The problem of targeting offerings to consumer taste is a difficult one to solve in a way that maximizes consumer goodwill and minimizes merchant expenses. Consumers generally want merchants or content providers to make accurate and helpful suggestions about what the viewer might like, but without inconveniencing the viewer by requiring the viewer to fill out extensive surveys or communicate at length with the merchant or content provider.

The ability to establish a profile of a viewer's habits or tastes benefits advertisers, merchants, and consumers alike. Advertisers achieve a competitive advantage by targeting ads to favorable viewers, receiving a higher response rate and using expensive advertising space more efficiently. Merchants can suggest a purchase that a viewer might need without having realized the need, and increase their sales significantly. The consumer benefits by being subjected to fewer advertisements that are irrelevant to the consumer, and possibly being exposed to products that fit the consumer's tastes which the viewer was not aware of.

Existing methods for establishing a consumer taste profile focus on the consumer's past actions and interactions with a provider. For example, a consumer's purchase of an item may be used to suggest more items like the purchased item. A consumer's rating of the purchased item through an online review website or feedback form may be used to further adjust a taste profile positively or negatively for the item. A consumer who views one online video may be encouraged to watch a sequel after the video is complete, or another video in the same genre. A consumer who views a product's webpage may have the item associated with the consumer's taste profile even if the viewer does not purchase the item, on the theory that the consumer is currently researching items of the given type and intends to buy one in the near future.

A limitation of these existing methods is that without the consumer's active participation in a rating system or survey, it is impossible to tell whether the consumer enjoyed the purchase of the item, or the viewing of the video, or other use or consumption of media and products.

Providers may also attempt to proactively determine consumer tastes by sending surveys to consumers, interviewing consumers, or putting together focus groups to gauge consumer reaction to media and brands. These polling methods may be very expensive, and risk destroying consumer goodwill by annoying consumers with unwanted communications and demands on their time.

Thus, there is a need felt in the art for methods of accurately determining the desires of a consumer in a passive manner, without the consumer's conscious or active participation.

BRIEF SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below.

To overcome limitations in the prior art described above, and to overcome other limitations that will be apparent upon reading and understanding the present specification, aspects described herein are directed to using sensor readings from devices worn by a viewer, or otherwise monitoring a viewer, to determine the viewer's emotional response to a media element. For example, the sensor readings and other environmental information (e.g., time of day, temperature, etc.) can be monitored and accumulated to build a viewer profile of emotional responses, e.g., favorable and unfavorable responses, to particular media, programs, movies, brands, products, persons, etc.

The sensor readings may be used to determine viewer heartbeat, breathing, posture, movement, speech, perspiration, facial expression, speech, tone, volume, and any other physical factors that may, alone or in conjunction with any of the physical characteristics above, change in response to a strong emotional reaction and thus be indicative of the viewer's underlying positive or negative emotional response to a media element.

The viewer's emotional response, alone or in combination with the viewer profile, may be used to suggest media content, particular portions or scenes within content, information, products, offers, and advertisements to the viewer which are personally targeted and which do not require additional, and often undesirable, user inputs, such as requiring the user to rate, comment, or reply to surveys.

Suggestions and offers may include offers to record streaming media, to purchase media, to license media, to change a currently displayed and disfavored streaming media, to receive contextually relevant information about media, to purchase tickets to view a film, to purchase merchandise, to receive coupons for merchandise, to take advantage of temporarily deals for merchandise, or to select from among already-curated advertisements to view.

BRIEF DESCRIPTION OF THE DRAWINGS

A more complete understanding of aspects described herein and the advantages thereof may be acquired by referring to the following description in consideration of the accompanying drawings, in which like reference numbers indicate like features, and wherein:

FIGS. 9A and 9B depict an illustrative embodiment of using sensor data to determine that a viewer has moved away from a display showing media in which the viewer is interested and offering to continue display of the media on a new display for seamless viewing.

FIG. 10 depicts an illustrative embodiment of using sensor data to determine viewer interest in merchandise and offer coupons or other deals to the viewer for the merchandise.

DETAILED DESCRIPTION

In the following description of the various embodiments, reference is made to the accompanying drawings, which form a part hereof, and in which is shown by way of illustration various embodiments in which aspects described herein may be practiced. It is to be understood that other embodiments may be utilized and structural and functional modifications may be made without departing from the scope of the described aspects and embodiments. Aspects described herein are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged" and similar terms, is meant to include both direct and indirect mounting, connecting, coupling, positioning and engaging.

Figure 1:
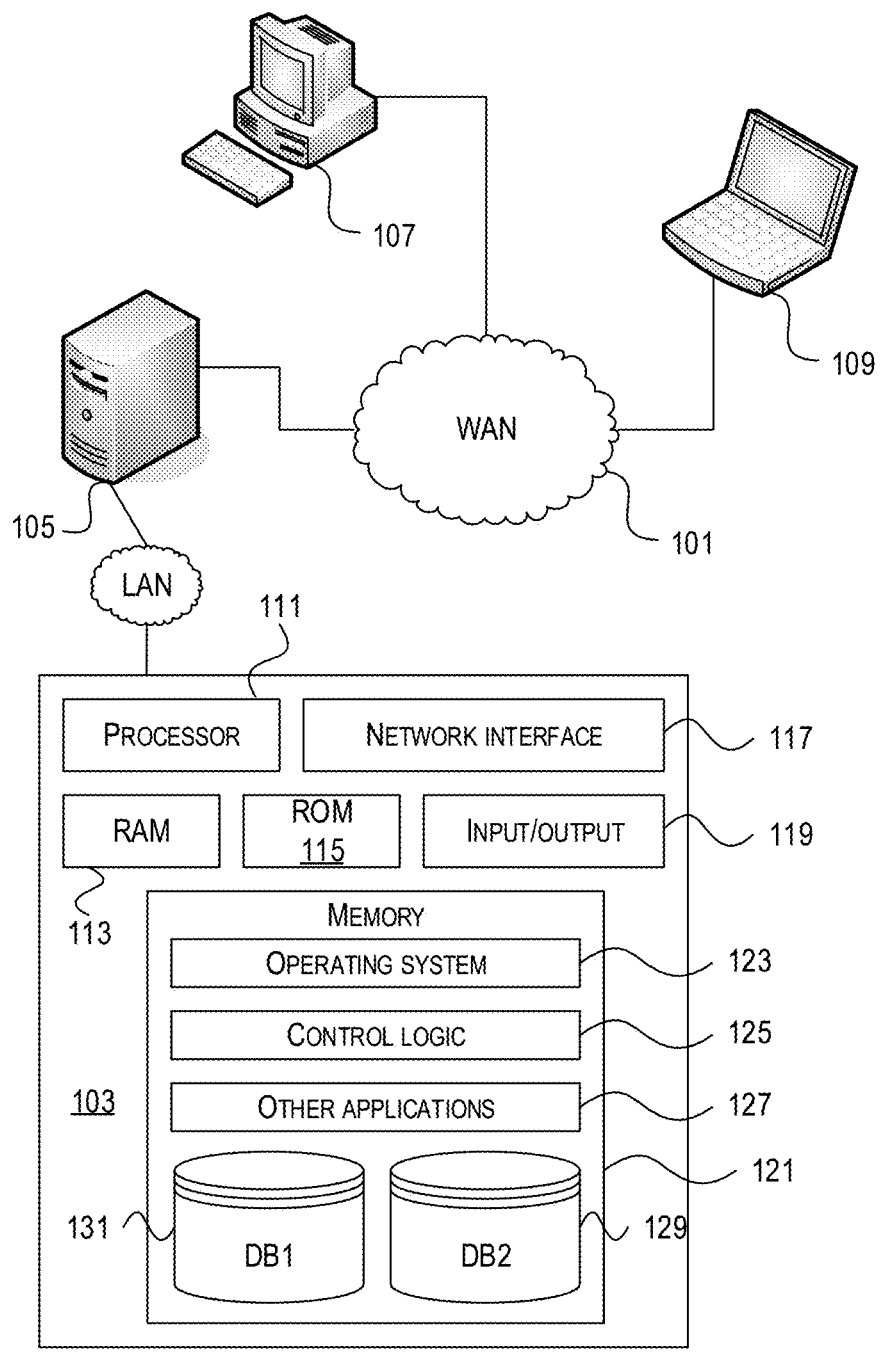
FIG. 1 depicts a computing environment in which one or more aspects described herein may be implemented.

FIG. 1 depicts one example of a network architecture and data processing device that may be used to implement one or more illustrative aspects described herein. Various network nodes 103, 105, 107, and 109 may be interconnected via a wide area network (WAN) 101, such as the Internet. Other networks may also or alternatively be used, including private intranets, corporate networks, LANs, wireless networks, personal networks (PAN), and the like. Network 101 is for illustration purposes and may be replaced with fewer or additional computer networks. A local area network (LAN) may have one or more of any known LAN topology and may use one or more of a variety of different protocols, such as Ethernet. Devices 103, 105, 107, 109 and other devices (not shown) may be connected to one or more of the networks via twisted pair wires, coaxial cable, fiber optics, radio waves or other communication media.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 103, web server 105, and client computers 107, 109. Data server 103 provides overall access, control and administration of databases and control software for performing one or more illustrative aspects described herein. Data server 103 may be connected to web server 105 through which viewers interact with and obtain data as requested. Alternatively, data server 103 may act as a web server itself and be directly connected to the Internet. Data server 103 may be connected to web server 105 through the network 101 (e.g., the Internet), via direct or indirect connection, or via some other network. Viewers may interact with the data server 103 using remote computers 107, 109, e.g., using a web browser to connect to the data server 103 via one or more externally exposed web sites hosted by web server 105. Client computers 107, 109 may be used in concert with data server 103 to access data stored therein, or may be used for other purposes. For example, from client device 107 a viewer may access web server 105 using an Internet browser, as is known in the art, or by executing a software application that communicates with web server 105 and/or data server 103 over a computer network (such as the Internet).

Servers and applications may be combined on the same physical machines, and retain separate virtual or logical addresses, or may reside on separate physical machines. FIG. 1 depicts just one example of a network architecture that may be used, and those of skill in the art will appreciate that the specific network architecture and data processing devices used may vary, and are secondary to the functionality that they provide, as further described herein. For example, services provided by web server 105 and data server 103 may be combined on a single server.

Each component 103, 105, 107, 109 may be any type of known computer, server, or data processing device. Data server 103, e.g., may include a processor 111 controlling overall operation of the rate server 103. Data server 103 may further include RAM 113, ROM 115, network interface 117, input/output interfaces 119 (e.g., keyboard, mouse, display, printer, etc.), and memory 121. I/O 119 may include a variety of interface units and drives for reading, writing, displaying, and/or printing data or files. Memory 121 may further store operating system software 123 for controlling overall operation of the data processing device 103, control logic 125 for instructing data server 103 to perform aspects described herein, and other application software 127 providing secondary, support, and/or other functionality which may or may not be used in conjunction with other aspects described herein. The control logic may also be referred to herein as the data server software 125. Functionality of the data server software may refer to operations or decisions made automatically based on rules coded into the control logic, made manually by a viewer providing input into the system, and/or a combination of automatic processing based on viewer input (e.g., queries, data updates, etc.).

Memory 121 may also store data used in performance of one or more aspects described herein, including a first database 129 and a second database 131. In some embodiments, the first database may include the second database (e.g., as a separate table, report, etc.). That is, the information can be stored in a single database, or separated into different logical, virtual, or physical databases, depending on system design. Devices 105, 107, 109 may have similar or different architecture as described with respect to device 103. Those of skill in the art will appreciate that the functionality of data processing device 103 (or device 105, 107, 109) as described herein may be spread across multiple data processing devices, for example, to distribute processing load across multiple computers, to segregate transactions based on geographic location, viewer access level, quality of service (QoS), etc.

One or more aspects described herein may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects, and such data structures are contemplated within the scope of computer executable instructions and computer-usable data described herein.

Figure 2:
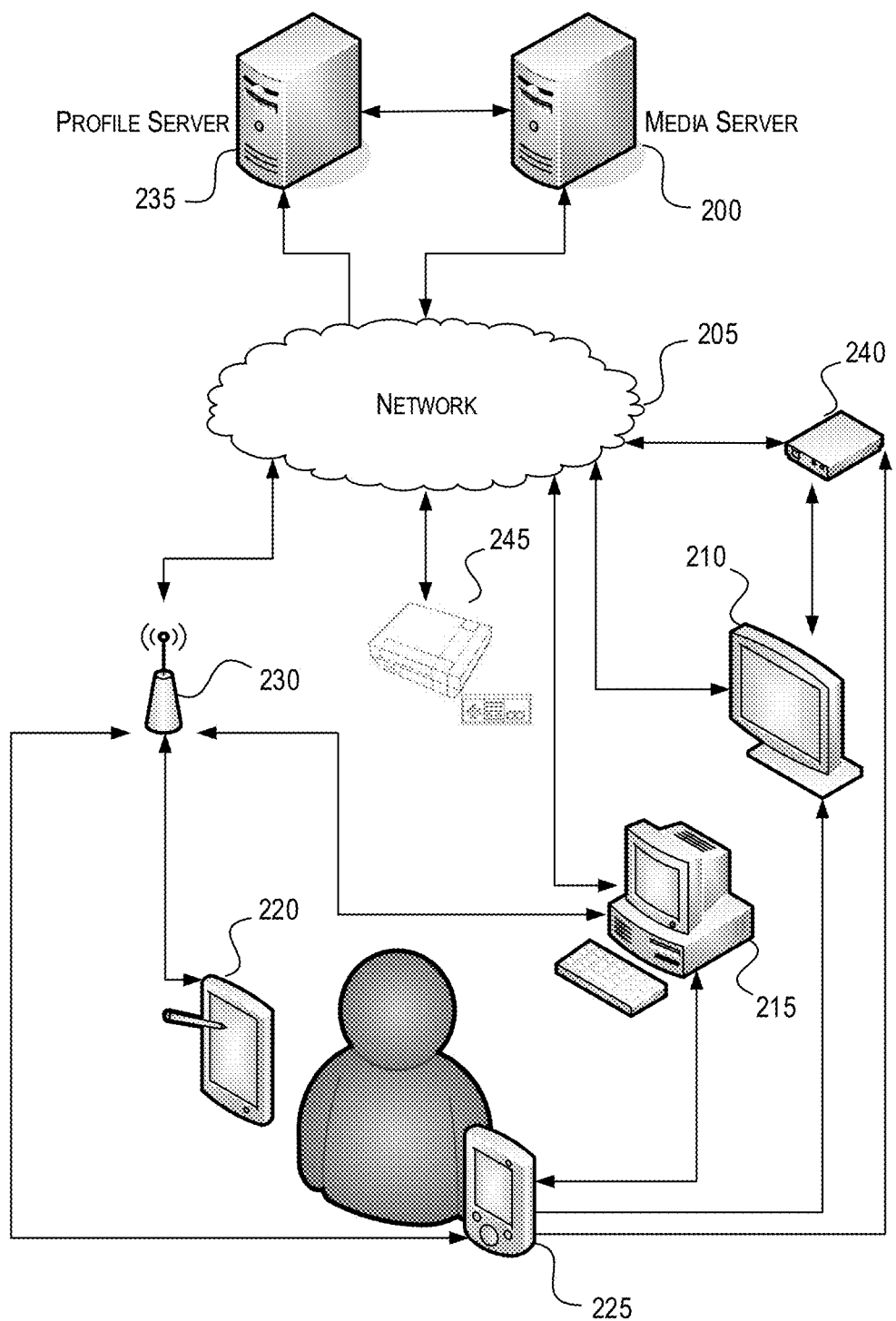
FIG. 2 depicts a system of connected computing devices, displays, and sensors which may be used to implement one or more aspects described herein.

FIG. 2 depicts a system of connected computing devices which may be used to implement one or more aspects described herein.

A computing device, such as media server 200, may transmit various media elements through a network 205 for eventual consumption by a viewer. Media server 200 may be a web server sending webpages, images, streaming video, social media pages, or other files through network 205 to a viewer's computing device 215. Media server 200 may be a head end sending a video stream via cable to a set top box 240 in a viewer's home, for display on television 210. Media server 200 may be a server that facilitates an online computer game and transmits data to the viewer in-game as the viewer plays on computing device 215 or gaming console 245.

Multiple devices may display media received from media server 200 to the viewer. Display 210 may be a television or other display connected directly to network 205 or may be a television connected to a cable network via set top box 208. Computing device 215 may be a desktop computer, laptop computer, or other computing device, and may be connected to network 205 directly, or may be connected wirelessly via wireless access point 230. Portable computing device 220 may be a tablet computer, personal digital assistant (PDA), cellular phone, or smart phone, and may be connected to network 205 by wireless access point 230 or by mobile broadband such as 3G, 4G, or LTE. Wireless access point 230 may be a wireless router, hotspot, cell tower, repeater, or any other device that facilitates a data connection.

Device 225 may be a smart phone, console game controller, television remote control, tablet computer, activity tracking device, sleep tracking device, wristband computing device, digital watch, or other wearable device. It may be worn by, attached to, or kept in close proximity to the viewer while the viewer is using any of devices 210, 215, 220, or 245. It may have sensors including, but not limited to, multiple-axis accelerometers, gyroscope, thermometer, galvanometer, pressure sensor, mass spectrometer, microphone, camera, global positioning system (GPS), or motion sensor, or may be connected to peripheral devices with one or more such sensors. Devices 210, 215, 220, and 245 may also incorporate one or more of these sensors, and the viewer may also be observed by other sensors, such as cameras of a home security system, or sensors in an automobile.

Sensors in devices 210, 215, 220, 225, and 245, and other sensors may be able to determine a variety of physical attributes of the viewer. For example, accelerometers, pressure sensors, or other sensors in a device in contact with the viewer or worn by the viewer may be able to sense the viewer's pulse and determine the viewer's heart rate. Accelerometers, pressure sensors, or other sensors may also be able to determine the viewer's breathing rate, the depth or shallowness of the viewer's breaths, or sharp intakes or exhalations of breath. A galvanometer or other sensor may be able to determine that the viewer is or is not perspiring. A thermometer, infrared camera, or other sensor may be able to detect minute changes in the viewer's core body temperature or in the temperature of particular parts of the body such as the face. A mass spectrometer or other sensor may be able to detect hormones or pheromones released in or from the viewer's body. Accelerometers, cameras, motion sensors, pressure sensors, or other sensors may be able to detect body movements or gestures by the viewer. A pressure sensor or other sensor may be able to detect tension in the viewer's body, such as a clenched first or a contracted muscle. A camera or other sensor may be able to detect the viewer's posture or facial expression. A microphone or other sensor may be able to detect the volume, pitch, tone, or content of the viewer's speech or other verbalizations. A global positioning system (GPS) sensor may be used to determine the viewer's location.

Devices 210, 215, 220, 225, and 245 may also be configured to receive viewer input in the form of pressing a button, touching a touchscreen, using a stylus on a touchscreen, manipulating a switch or joystick, shaking a controller to activate an accelerometer, moving a mouse cursor, clicking with a mouse, or control via voice commands.

Devices 210, 215, 220, 225, and 245 and any other sensors may use network 205 directly or indirectly transmit sensor and input data, along with precise timestamps of when the data was recorded, to a computing device, such as a profile server 235. The computing device may store a database of viewer information, media information, and sensor information.

Figure 3:
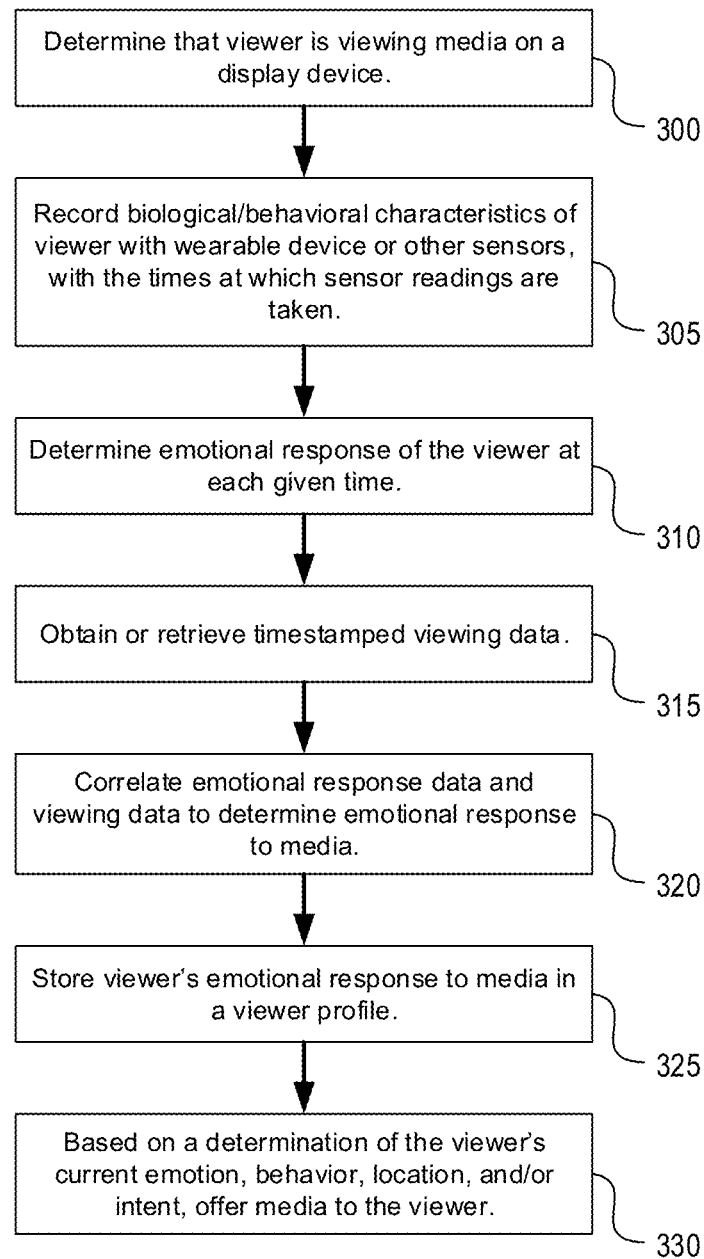
FIG. 3 depicts a method for determining an emotional response of a viewer based on observations of that viewer while consuming media, according to one or more aspects described herein.

FIG. 3 depicts aspects of an embodiment. In step 300, the determination may be made that a viewer is consuming media on a display device. This determination may be made either by transmitting the media to the viewer directly, or by collaborating with a content provider that allows an interface for querying the current media consumption behavior (such as a content provider who shares viewer information with advertisers).

In step 305, the sensors in devices 210, 215, 220, 225, and 245 and any other sensors may monitor sensor data at regular intervals, such as multiple times per second, every second, or after a predetermined number of seconds. The precise time of the sensor record may also be stored. Alternatively, the sensors may store sensor data only with there is a change in a sensor reading compared to a previous observation, rather than storing a same value at repeated intervals.

The sensors may also record corresponding environmental characteristics, such as time of day (as measured by an internal clock), light level (as measured by an optical sensor), temperature (as measured by a thermometer), location (as measured by global positioning system (GPS) sensor), weather events (such as lightning, thunder, rain, hail, snow, tornado, or hurricane, as measured by crossreferencing a GPS reading with a weather report database). Environmental characteristics may be later used to eliminate false positive or false negative readings, such as a determination that a person was angry upon viewing media because of increased temperature being discounted if the person is in an area with abnormally high heat, or a determination that a person was fearful after viewing media being discounted if there was a tornado warning in effect at the time.

The recorded sensor data and timestamps of the data may be transmitted to a computing device, such as a profile server 235. If analysis of raw sensor data is needed to understand its significance, such as transforming raw audio data into a transcript of spoken words, or transforming raw accelerometer data into the gesture it signifies, the analysis may be performed at the sensor before transmission, at the computing device itself, or at an intermediate device.

In step 310, computing device 235 may attempt to determine an emotional response which the sensor data signifies at each recorded time.

For example, intense excitement and interest in what is being viewed may be determined upon a sensor reading of physical attributes or behavior showing any of increased heart rate, holding breath, being silent, speaking rapidly, particular speech content and vocalizations (such as "Ooh!" or "Ah!" or "Neat!"), holding still, leaning forward or onto the edge of a seat, or a combination of these or of other factors known in the psychological or medicinal arts to indicate excitement.

Happiness or amusement may be determined upon a sensor reading of physical attributes or behavior showing any of laughter, a smiling facial expression, particular speech content that contains positively connoted words, relaxation of muscles, or a combination of these or of other factors known in the psychological or medicinal arts to indicate happiness.

Fear may be determined upon a sensor reading of physical attributes or behavior showing any of increased heart rate, shaking or trembling, sweating/perspiration, increased pitch of voice, particular speech content with key words such as "Scary!", gasping, a facial expression of fear, sensation of symptoms associated with adrenaline or a "fight or flight" reaction, sensation of fear-induced pheromones, or a combination of these or of other factors known in the psychological or medicinal arts to indicate fear.

Disinterest or apathy may be determined upon a sensor reading of physical attributes or behavior showing any of restless movement, speaking in a normal voice, speaking over the sound of the media, a bored tone, speech content with keywords like "bored", lack of eye contact with currently playing media, a relaxed/apathetic facial expression sensed to correlate with boredom, or a combination of these or of other factors known in the psychological or medicinal arts to indicate disinterest.

Anger or antipathy may be determined upon a sensor reading of physical attributes or behavior showing any of increased body temperature, increased volume, speech content with negatively connoted or offensive keywords, tone of voice, agitated movement, or tension in muscles, or a combination of these or of other factors known in the psychological or medicinal arts to indicate anger.

Other emotions, such as sadness, disgust, affection, or suspicion, may be determinable by facial expression, tone of voice, speech content and the detection of keywords or sentiments therein, or other physical attributes or behavior known in the psychological or medicinal arts to indicate an emotion.

Emotional responses may be determined either by a persistent sensor reading (such as continuing to determine a smiling facial expression over a period of time) or may be determined only in response to a change in sensor reading (such that beginning to perspire indicates an emotion, but continuing to sense unevaporated perspiration does not). A change in sensor readings may be deemed significant based on an absolute change (such as an increase in heart rate of 20 or more beats per minute), a relative change (such as a 15% or more increase in heart rate), or a reference to a historical or typical value (elevated, but returning to "normal").

In step 315, computing device 235 may obtain or retrieve the viewer's media consumption data. The computing device may transmit a request to another computing device, such as media server 200, to share what media the viewer was consuming at each timestamp for which an emotional state has been determined. For example, if other computing device 200 is a web server, it may know which web page or other online content was sent to the viewer's browser immediately before a given timestamp. If other computing device 200 is a head end, it may know what TV program, film, commercial advertisement, or other offering was being displayed to the viewer's television by a set top box. Other computing device 200 may have means for determining what programs the viewer is using on a computer, what page of what e-book is being read by the viewer, or what apps are being used on a smartphone by the viewer at a given time.

Additionally, other computing device 200 may have access to the manner in which the viewer obtained access to the media the viewer was viewing. For example, a viewer who has paid for access to the media specifically—such as by purchasing a cable television show "on demand", purchasing a ticket to a movie theater, purchasing or renting video content through an online distributor, or ordering physical media from an online merchant—may be determined to have elevated interest in the media or in actors or other elements featured in the media, and this elevated interest can be combined with the biometric feedback data in determining a positive emotional response to the media or those actors or other elements featured in the media at the time of the biometric feedback indicating positive emotional response. A viewer who has incurred a cost other than directly paying for the media, such as choosing to watch free media with interspersed mandatory advertisements, or paying for a subscription to a service with many available media for consumption, may be determined to have an equally elevated interest as for a direct purchase, a less elevated interest, or no additional interest at all compared to media for which the viewer incurred no cost.

In step 320, computing device 235 may take the compilations of viewer emotion at points in time and viewer media use at those same points in time to determine the viewer's emotional responses to the media element that the viewer was consuming at the time of the sensor reading. The granularity of the determination may be limited to a viewer reaction to an entire show or movie as a whole, or increased, such as by determining the viewer response to a particular scene in a program, or determining viewer response to a particular brand or item in an advertisement.

In step 325, computing device 235 may, optionally, store the determination in a database with records that associate a viewer, a media element, and an emotion by the viewer to the media element. In some embodiments where the disclosed methods involve real time processing, storing may not be necessary. The media elements for which emotions are monitored, detected, analyzed and/or stored may be entire items of content, such as shows or movies, or portions of content. For example, a viewer may have a stored association with an entire television series, such as M*A*S*H, or with a particular episode, such as the M*A*S*H series finale, or with a series of movies, such as the Rocky series, or only a particular movie, such as Rocky IV. A viewer may have a stored positive association to a particular season of a television show, such as the first season of Arrow, while having a stored negative association with another season of the same television show, such as the fourth season of Arrow.

Media elements may also be or comprise specific items, brands, scenes, persons, or other elements which are found in content that is presented when sensor readings are recorded. For example, a viewer may have a stored emotional reaction to a character, like Darth Vader, and have a separate emotional reaction for an actor who plays the character, like James Earl Jones. A viewer may have a stored emotional reaction to a type of vehicle, like an airplane or sports car, or a specific manufacturer, such as Lockheed Martin or Porsche. A viewer may have a positive stored emotional reaction to a scene, such as the "I'll have what she's having" scene from When Harry Met Sally, while remaining neutral or even negative to the film as a whole, or to the two actors involved, Billy Crystal and Meg Ryan. A viewer may have a strongly negative stored emotional reaction to guns or gunfire regardless of the genre or actors involved. A viewer may have a positive stored emotional reaction to animals featured in a film, or to particular species or breeds of animals. A viewer may have a positive stored emotional reaction to a genre such as "western" or "murder mystery." A viewer may have a positive stored emotional reaction to a particular food, such as tacos, or to a restaurant brand, food brand, or beverage brand featured in media content. These records may be compiled into a comprehensive viewer profile that stores and tracks viewer emotional responses to a wide variety of possible inputs.

In step 330, the stored records and/or viewer profile may be used to offer a media element to the viewer. Selection of the media element may be based on past positive reactions to that element, past positive reactions to similar elements, past negative reactions to other elements, a currently sensed emotional state of the viewer, currently observed behavior of the viewer, the location of the viewer, which displays or devices the viewer is currently using, or any combination of these factors. Computing devices 200 or 235 may then transmit to the viewer a notification that the selected media is available for consumption, purchase, or other use.

In an alternative embodiment, a group of viewers may be watching a display simultaneously, each of whom may be individually currently sensed by a wearable device sensor or may have been individually sensed by a wearable device sensor in the past to establish an emotional profile on computing device 235. Computing devices 200 and/or 235 may determine that each member of the group is watching the same display, and the current information from the sensors and/or past information from emotional profiles of multiple viewers may be combined to make a recommendation to the entire group and notify them that selected media is available for consumption, purchase, or other use.

Selection for a group may be based on minimizing negative expected reaction to the selection across the group, maximizing positive expected reaction to the selection across the group, maximizing positive expected reaction under the constraint that no viewer has an expected negative reaction, or another metric. Selection may also be based upon selecting a media containing elements each of which at least one viewer has an expected positive reaction to. For example, if a first viewer has been determined to enjoy Sean Connery while a second viewer likes sports cars, a James Bond film containing both may be suggested. If the second viewer likes the actor Alec Baldwin or likes sailing instead of sports cars, the film The Hunt For Red October might be suggested instead.

In the foregoing embodiments, the roles of the computing devices 200 and 235 may be filled by two distinct devices, a single device, or a multitude of modules spread across many devices, transmitting media data, sensor data, analysis of sensor data, or other data among themselves.

Figure 4:
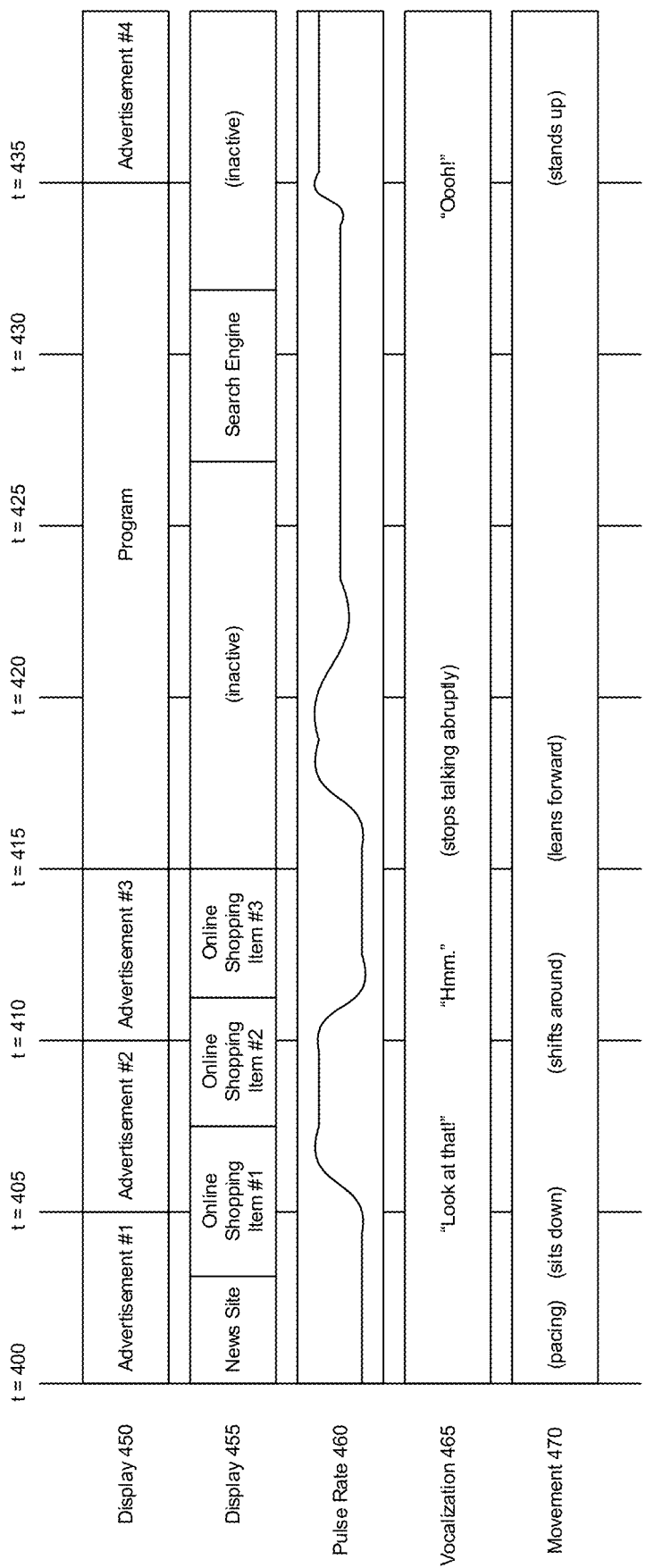
FIG. 4 depicts an illustrative set of sensor and media consumption data used to determine an emotional response of a viewer, according to one or more aspects described herein.

FIG. 4 depicts an example set of sensor and media data of a viewer's physical attributes which might be captured over a period of time for a viewer of multiple display devices.

At time 400, the viewer is browsing a news site on smartphone display 455 while Advertisement #1 begins playing on television display 450. The viewer's heart rate 460 is normal, audio sensor data analyzed to determine vocalizations 465 shows that the viewer is silent, and accelerometer and camera data analyzed to determine movement 470 shows the viewer is pacing around. Accordingly, computing device 235 may determine that the viewer was feeling disinterest at time 400, and was unimpressed by the news site and by Advertisement #1.

At time 405, the viewer is determined to sit down, and heart rate begins dramatically increasing. Microphone data is analyzed to determine that the viewer has shouted "Look at that!" Computing device 235 may determine that the viewer is now feeling extreme interest at time 405. By comparing with media information regarding displays 450 and 455, computing device 235 may determine that the viewer has an extreme interest in either Online Shopping Item #1, which is displayed on the smartphone, or an item in Advertisement #2, which is displayed on the television. The determination between the two may be made on the basis of location (the viewer is sitting in a chair directly in front of the television), movement (the viewer set down the smartphone before the exclamation), camera data (the viewer is making eye contact with the television), or order of events (the viewer was viewing the online item for a period of time before time 405 without reaction, but reacted immediately when the advertisement began at time 405). Computing device 235 may then update the viewer profile to record the viewer's interest in the item or brand advertised in Advertisement #2.

At time 410, the viewer shifts around after having been still, and heart rate begins to return to normal. Although heart rate has been elevated the entire time that the viewer has used a smartphone to display Online Shopping Item #2, the fact that heart rate did not increase during the time frame may be used to determine a lack of interest in Online Shopping Item #2. Likewise, the decreasing heart rate during viewing of Advertisement #3 and Online Shopping Item #3 may be used to determine disinterest in products displayed therein.

At time 415, the viewer turns off display 455 and turns his attention solely to a program on display 450. Shortly after the program begin, the viewer's detected heart rate elevates, the viewer is detected to lean forward, and the viewer, who might have been involved in a conversation, stops talking abruptly. These signals may be combined to determine that the viewer is intensely interested in the program that the viewer is currently viewing. Computing device 235 may request data from a head end, set top box, streaming media server, or other media provider to determine which program the viewer is watching. Once the program is identified, computing device 235 may create an entry recording that the viewer is intensely interested in the particular program which the viewer was watching.

At time 420, the viewer's heart rate begins to slow, allowing computing device 235 to determine that the intensity of the viewer's emotional reaction is decreasing. This determination may allow computing device 235 to increase the granularity of the records regarding the viewer, potentially showing that the viewer was interested in the previous scene at time 415 because it contained a particular actor, brand, or genre that is not present in a scene at time 420. Computing device 235 may then update its records to show interest by the viewer in both in the program and the actor, brand, or genre, or alternatively may replace the record of the program with the actor, brand, or genre. Repeated sensor determinations over many airings of a program may aid in determining what element in particular is generating interest by the viewer.

At time 425, the viewer's sensor data has stabilized at a slightly elevated heart rate and with no changes in posture or speech. The slightly elevated heart rate may be considered as evidence by computing device 235 of general interest in the program as a whole, or may be discounted as an artifact from the extreme increase in heart rate from a particular scene.

At time 430, the viewer has reactivated display 455 and is using it to operate a search engine. This information may be used by computing device 235 to determine that the viewer's interest in the program has waned enough that the user is distracted by other devices. Alternatively, computing device 235 may be able to determine the queries that the viewer was entering into the search engine. Queries related to the program on display 450 may be used to determine that the viewer is still highly interested in the program despite presently paying attention to a different device.

At time 435, the program on display 450 is coming to a close, and the viewer has a spiking heart rate, is not focused on another display, and says "Oooh!" These factors may again be used by computing device 235 to determine intense interest in the program by the viewer, perhaps in response to a "cliffhanger" ending to the program. Although the user's heart rate remains elevated for a subsequent time, computing device 235 may determine that the viewer is not interested in the following Advertisement #4, discounting the heart rate as an artifact from the program, and considering the additional determination that the viewer stands up after time 435 and may not even be viewing display 450 after standing up.

FIGS. 5-10 illustrate a series of embodiments provided merely to demonstrate the variety of applications of the novel matter herein. They in no way circumscribe or limit the scope of the claims or of other embodiments.

Figure 5:
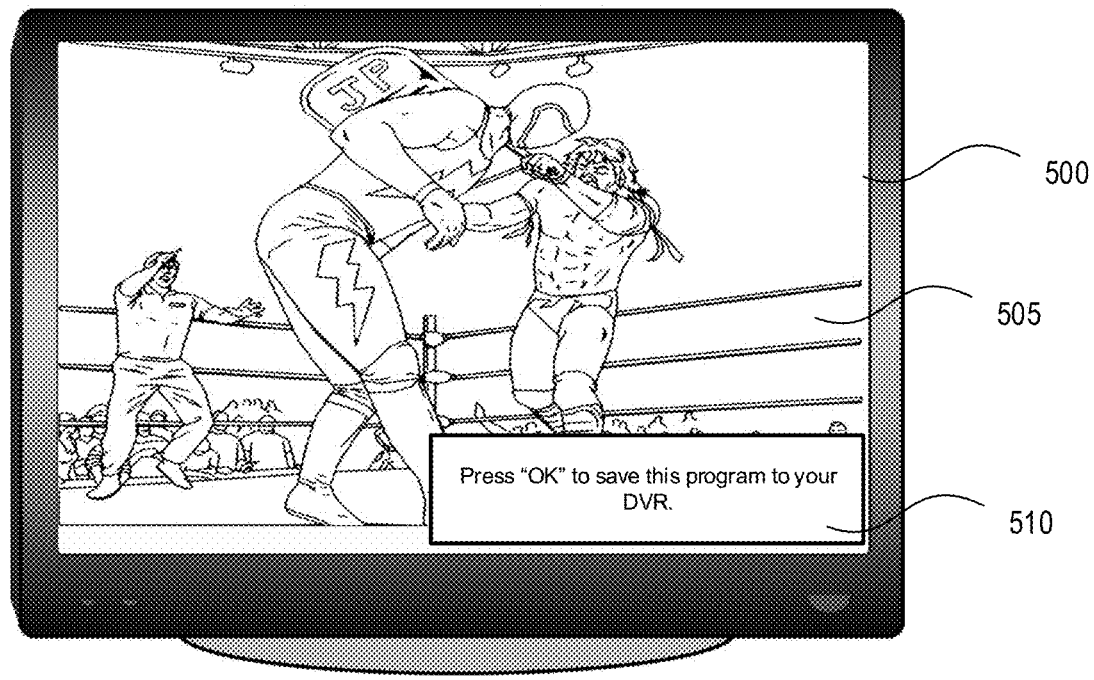
FIG. 5 depicts an illustrative embodiment of using sensor data to offer recording of media in which the viewer is interested.

FIG. 5 depicts one embodiment, wherein physical characteristics of the viewer—such as viewer heartbeat, breathing, posture, movement, speech, perspiration, facial expression, speech, tone, and volume—may be monitored by one or more wearable biometric sensors while watching a streaming media program 505, such as a wrestling match, on display 500. The sensors may send the sensor readings to computing device 235, which may cross-reference the sensor data with records from the viewer's television provider, and may immediately determine that the viewer is experiencing a positive reaction to the program, such as excitement or happiness. Computing device 235 or 200 may determine that the viewer owns a device capable of recording input to display 500 or recording input to a set top box that controls the display. The display 500 may then be caused to display a message 510 to the viewer such as "Press 'OK' to save this program to your DVR." The viewer might then be able to press a button on a remote control or set top box controller, which may be configured to record the remainder or the entirety of the program to the recording device for later display.

Alternatively, computing device 235 may determine that the viewer is currently holding a mobile device, and cause message 510 to be displayed on the mobile device display instead. Tapping or otherwise interacting with the message may cause the mobile device to communicate the viewer's selection to computing device 235, which may then cause the recording device to record a portion of the program, the remainder of the program, or the entirety of the program. Tapping or otherwise interacting with the message may cause the mobile device to communicate directly with the set top box or other recording device to cause recording of the program.

Figure 6:
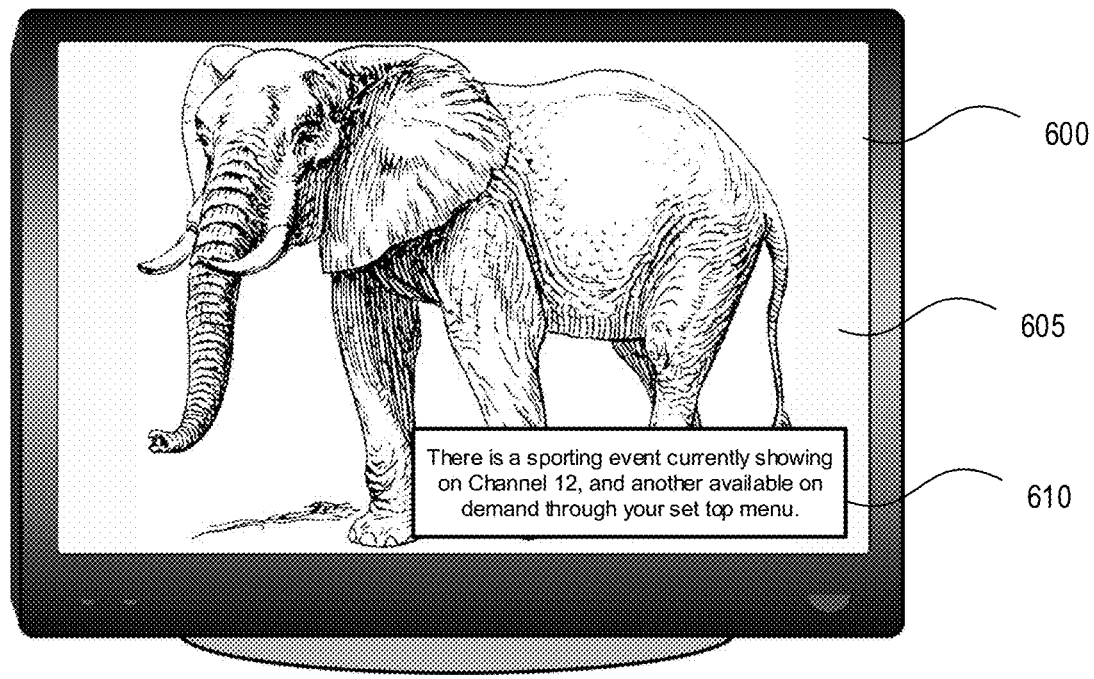
FIG. 6 depicts an illustrative embodiment of using sensor data to offer alternative media to media in which the viewer is interested.

FIG. 6 depicts another embodiment, wherein the viewer may be monitored by wearable biometric sensors while watching another streaming media program 605, such as a nature documentary, on display 600. The sensors may send sensor readings to computing device 235, which may cross-reference the sensor readings with records from the viewer's television provider, internet service provider, cellular network provider, or the like, and may immediately determine that the viewer is experiencing a negative reaction to program 605, such as boredom or disgust.

Computing device 235 may then determine a list of program offerings currently available to the viewer, for example being broadcast for pickup by antenna, available under the viewer's television subscription plan, or freely available online. Computing device 235 may then select an available program to offer instead. The selection may be based on the viewer's existing profile, selecting a program like one to which the viewer expressed a positive emotional reaction in the past, or may be based on merely selecting a program to which no negative emotional reaction has been expressed in the past. Computing device 235 may then cause display 600 to display a message 610 informing the viewer that a preferable program is available. The message may simply inform the viewer of the existence of the preferable program, or may allow the viewer to press a button or issue a command to immediately display the preferable program instead of the current program.

Alternatively, computing device 235 may determine that the viewer is currently holding a mobile device, and cause message 610 to be displayed on the mobile device display instead. Tapping the message may cause the mobile device to communicate the action directly to a set top box to change the currently displayed program, or may communicate with computing device 235, which may directly or indirectly cause the display to change the currently displayed program.

Figure 7:
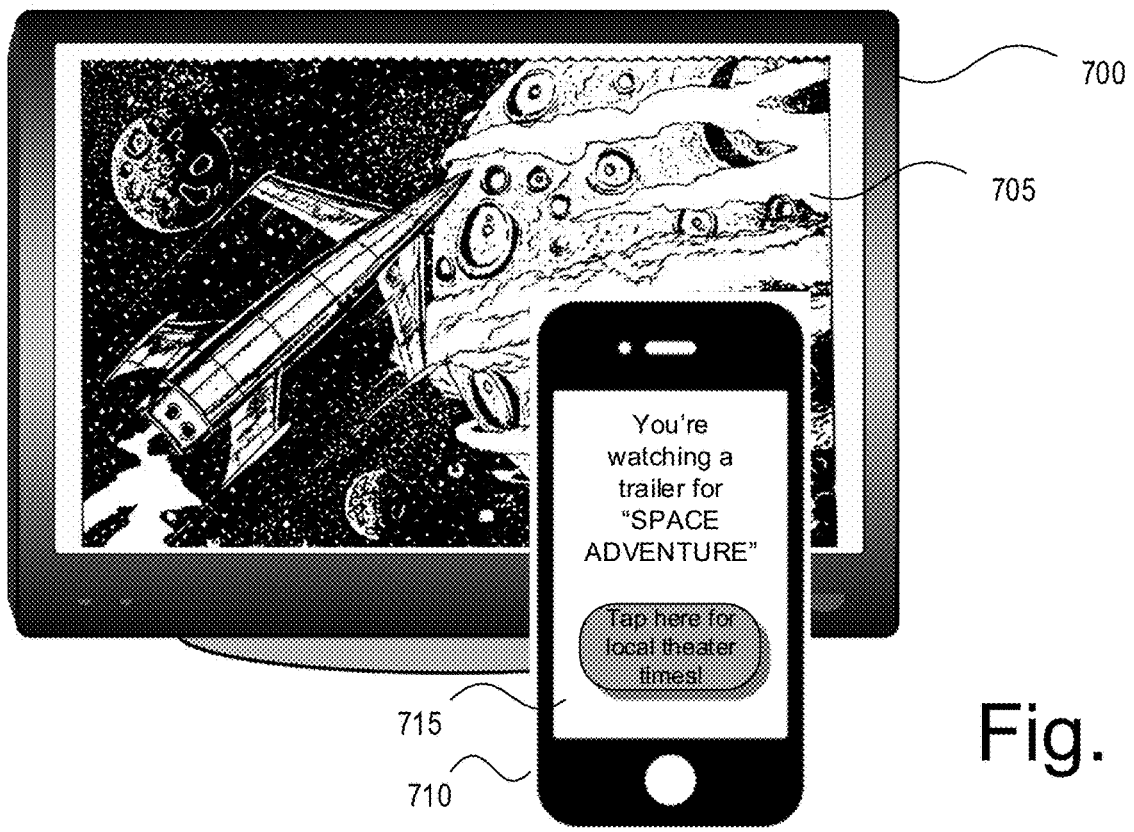
FIG. 7 depicts an illustrative embodiment of using sensor data to offer contextually relevant information about a media in which the viewer is interested.

FIG. 7 depicts another embodiment, wherein the viewer may be monitored by sensors while watching media element 705 on display 700. The sensors may send sensor readings to computing device 235, which may cross-reference the sensor readings with records from the viewer's television provider, internet service provider, cellular network provider, or the like, and may immediately determine that the viewer is demonstrating interest in media element 705. Computing device 235 may then determine that there is contextually related information about media element 705 which the viewer may be interested in. Computing device 235 may then cause display 700 or mobile device 710 to display message 715 with the contextually related information, or with a link to the information.

If the media element is an advertisement, for example, the message 715 may include a hyperlink to a web page for the product being advertised, a web page for an online merchant selling the product, the web page of the company which makes the product, or a notification of nearby stores determined to stock the product. If the media element is a trailer for a movie, the message may include a list of theaters and times where the movie will be shown, a hyperlink to a promotional web page for the movie, or a hyperlink to a third party web page or database with information about the movie. If the media element is a political advertisement, the message may include a hyperlink to a candidate's or party's web site, or an interactive message that allows the viewer to enter financial details for donation to a candidate or to sign up for a candidate's mailing list or consent to future communications from the candidate.

Figure 8:
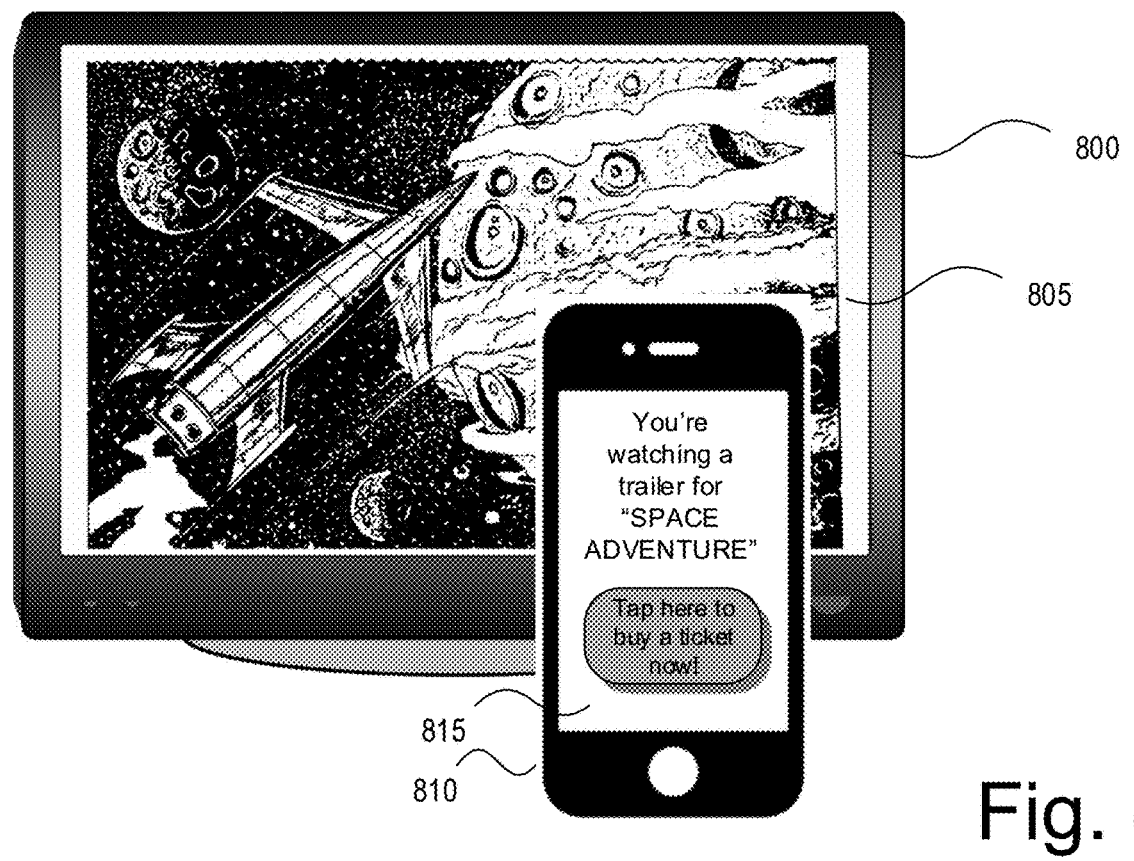
FIG. 8 depicts an illustrative embodiment of using sensor data to determine viewer interest in a movie and offer to sell tickets to that movie to the viewer.

FIG. 8 depicts another embodiment, wherein the viewer may be recorded by sensors while watching movie trailer 805 on display 800. The sensors may send sensor readings to computing device 235, which may cross-reference the sensor readings with records from the viewer's television provider, internet service provider, cellular network provider, or the like, and may immediately determine that the viewer is demonstrating interest in movie trailer 805. Computing device 235 may also determine the viewer's location, and cross-reference the movie in which the viewer demonstrates interest with local theater offerings and times.

Computing device 235 may determine that the viewer is currently wearing or holding mobile display 810, and may cause message 815 to be displayed on the mobile display. The message 815 may inform the viewer that tickets to the movie advertised are available for purchase, and may include a hyperlink to an online merchant page that sells tickets to the movie advertised. The message may also inform the viewer that there is a coupon or a special deal being offered to obtain the tickets at a reduced price. Alternatively, computing device 235 may determine that display 800 is a device capable of displaying web pages, and may cause message 815 to be displayed directly on display 800.

FIGS. 9a and 9b depict another embodiment, wherein the viewer may be recorded by sensors while watching media 905 on display 900. The sensors may send sensor readings to computing device 235, which may cross-reference the sensor readings with records from the viewer's television provider, internet service provider, cellular network provider, or the like, and may immediately determine that the viewer is demonstrating interest in media 905. The sensors may be used to then determine (for example, by accelerometer, motion sensor, global positioning system (GPS), or a camera) that the viewer has physically moved away from display 900. Computing device 235 may then cause a message to be displayed on mobile device 910. The message may indicate that the viewer may tap the message or otherwise input a command to continue watching media 905 on mobile device 910 while away from display 900. Computing device 235 or another server may receive the viewer input and cause mobile device 910 to display media 905.

The sensors may additionally be used to determine that the viewer has returned to display 900 and will be able to observe it again. In response, computing device 235 may be configured to automatically cause mobile device 910 to cease play media 905 and may automatically cause display 900 to continue to play media 905, so that the viewer has a seamless viewing experience regardless of location. Alternatively, computing device 235 may be configured to respond to determining that the viewer has returned to display 900 by sending a message offering to terminate media playback on mobile device 910, and not continue playback on display 900 unless or until the viewer indicates via input response to the message that the viewer wants to return to display 900

Alternatively, the viewer may begin watching media on mobile device 910, may be determined to have a positive reaction to the media, and then be determined to have approached display 900. Computing device 235 may be configured to respond by automatically displaying a message on mobile device 910 that the media may now be displayed on display 900 instead. In response to an input response from the viewer, computing device 235 may then cause display 900 to begin playing the media at the same point in time, and may cause mobile device 910 to cease playing the media. Alternatively, computing device 235 may be configured to automatically cause the media to display on display 900 and to stop displaying on mobile device 910, in response to the viewer's pre-selection of an option to automatically transfer media between viewing devices.

FIG. 10 depicts another embodiment, wherein the viewer may be recorded by sensors after entering a store and beginning to look at merchandise 1000, such as a particular piece of clothing, offered for sale. The sensors may be capable of determining the user's current location, for example via GPS sensor or other location sensing system. The sensors may additionally be capable of sensing radio frequency identification (RFID) tags or other communication devices affixed to merchandise 1000, affixed to other merchandise, or placed throughout the store. The sensors may send sensor readings to computing device 235, which may cross-reference the sensor readings with maps of merchants, databases associating particular RFID tag or other tag information with merchants or merchandise, or other information regarding merchants and merchandise. Computing device 235 may then be able to determine that the viewer is demonstrating interest in merchandise 1000 or in the store generally. Computing device 235 may instead have previously determined an interest in merchandise 1000 due to the viewer's reaction to media featuring merchandise 1000 or other brands on media consumed by the viewer in the viewer's home.

Computing device 235 may be configured to respond to this determination by causing a message 1010 to display on mobile device 1005. Message 1010 may offer a coupon to purchase merchandise 1000 at a reduced price, may alert the user that the merchandise is available only for a limited time, may offer a coupon for merchandise at the store generally, may inform the viewer of currently-offered deals that require the purchase of merchandise 1000 as a prerequisite to receive another benefit or that result in receiving merchandise 1000 for free or for a reduced price, or may inform the viewer of all currently-offered deals at the store.

Computing device 235 may additionally cause the display of or offer display of other relevant information to the viewer in response to the determination of the viewer's location and interest. Computing device 235 may cause display of hyperlinks to web pages of the manufacturer or designer of merchandise 1000 or other relevant merchandise, hyperlinks to web pages with reviews of merchandise 1000 or other relevant merchandise, or hyperlinks to an online merchant who also sells merchandise 1000 or other relevant merchandise.

Instead of or additionally to causing display of a message on mobile device 1005 while the viewer is present in the store, computing device 235 may update the viewer's emotional response profile and may at a future time display an offer to sell merchandise 1000 to the viewer, remind the viewer that merchandise 1000 is still available for sale, or link the viewer to an online merchant who sells merchandise 1000.

In another embodiment, media may be offered for sale or rent to a viewer. The viewer may be recorded by sensors while watching a program advertisement on a display. The sensors may send the readings to computing device 235, which may cross-reference the sensor data with records from the viewer's television provider, and may immediately determine that the viewer is experiencing a positive reaction to the advertisement, such as excitement or happiness. Computing device 235 may determine that the viewer is capable of purchasing the rights to view the program being advertised, such as through pay-per-view, video on demand, rental through a third party, or a paid video download. Computing device 235 may then cause a display associated with the viewer to alert the viewer that purchase, rental, or licensing of the program is available, and may include a link to an online merchant to which the viewer may go in order to do so.

In another embodiment, targeted advertising may be improved. Computing device 235 may transmit previously determined information regarding a viewer's emotional responses to particular media elements, or even a viewer's complete emotional response profile, to another computing device, such as an advertising server. The advertising server may then use the transmitted information to determine what advertisements to insert in media later viewed by the viewer. The advertising server may insert advertisements into web pages, into mobile applications, into streaming video, within television programs, during commercial breaks between parts of television programs, or in any other medium that may be observed by a viewer. The insertion may instead be performed by media server in response to instructions from the advertising server.

The advertising server may determine which advertisement to insert based on an advertisement containing elements which have been determined to elicit a positive reaction from the viewer, based on an advertisement containing elements similar to those determined to elicit a positive reaction from the viewer in the past, or based on an advertisement not containing elements which have been determined to elicit a negative reaction in the past.

The advertising server may also display a message to the viewer before displaying any advertisements, offering the viewer a choice between two or more advertisements which are determined to be likely to be viewed positively by the viewer. The viewer may select one of the advertisements to view by clicking, pressing a button, or otherwise indicating input which is relayed to the advertising server. The advertisement server may then cause the selected advertisement to be shown to the viewer. Alternatively, the advertising server may display one advertisement by default, but may include a message to the viewer that a different advertisement is available for viewing. The viewer may click, press a button, or communicate other input to the advertisement server to cause the second advertisement to be displayed instead.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A method comprising:
   receiving, by a computing device, a timestamp associated with a first media element displayed to a viewer and information indicating environmental characteristics of an environment associated with the viewer;
   receiving, at a time associated with the timestamp, information indicative of a change in one or more physical attributes of the viewer, wherein the one or more physical attributes comprise one or more of: a viewer position, a facial expression, or a sound output by the viewer;
   determining, based on the timestamp, content of the first media element displayed to the viewer;
   determining an emotional state, of the viewer, indicated by the change in the one or more physical attributes of the viewer;
   determining, based on determining that the emotional state is related to the content and unrelated to the environmental characteristics, a current level of interest of the viewer in the content at the time; and
   based on determining the current level of interest of the viewer in the content at the time and based on past reactions of the viewer to media elements and the first media element, sending a second media element to the viewer.

2. The method of claim 1, wherein the one or more physical attributes of the viewer are detected via sensors of a wearable device.

3. The method of claim 1, wherein:
   the determining the current level of interest of the viewer in the content comprises generating or amending a viewer interest profile;
   the sending the second media element comprises selecting the second media element based on the viewer interest profile; and
   the second media element comprises an offer to sell a good or service which was displayed in the first media element.

4. The method of claim 1, further comprising:
   prior to the sending the second media element to the viewer, offering to record content that the viewer can request for replay at a later date.

5. The method of claim 1, further comprising:
   prior to the sending the second media element to the viewer, notifying the viewer that the second media element is currently available from a media source, and offering to display the media source.

6. The method of claim 1, further comprising:
   prior to the sending the second media element to the viewer, notifying the viewer that media can be displayed on-demand to the viewer.

7. The method of claim 1, wherein the first media element is displayed to the viewer on a first display, and the second media element is displayed on a second display different from the first display.

8. The method of claim 1, further comprising:
   prior to the sending the second media element to the viewer, notifying the viewer that the second media element is available for purchase or license.

9. The method of claim 1, wherein the sending the second media element is additionally based at least in part on a viewer's determined location.

10. The method of claim 1, wherein:
   the viewer position comprises one or more of posture, standing, or sitting;

the facial expression comprises one or more of smiling, a fearful facial expression, or a relaxed facial expression; or the sound output by the viewer comprises one or more of speech rate, speech content, vocalizations, speech volume, or speech tone.

11. The method of claim 1, further comprising:
receiving information indicative of a second change in one or more second physical attributes of the viewer, wherein the one or more second physical attributes comprises one or more of a heart rate of the viewer or a breathing rate of the viewer,
wherein the determining the current level of interest of the viewer at the time is further determined based on the second change in the one or more second physical attributes.

12. The method of claim 1, further comprising:
receiving a second timestamp indicative of the time associated with the timestamp;
determining, based on the timestamp and the second timestamp, that the content of the first media element is associated with the current level of interest of the viewer at the time; and
selecting, based on the content of the first media element being associated with the current level of interest of the viewer at the time, the second media element.

13. The method of claim 1, wherein the past reactions comprise a positive reaction to a media element similar to the first media element.

14. The method of claim 1, further comprising determining that a second emotional state of the viewer is unrelated to second content and related to second environmental characteristics by:
determining that the second emotional state of the viewer comprises the viewer being angry;
determining that the second environmental characteristics indicate a temperature of the environment; and
determining that the viewer being angry is based on the temperature of the environment.

15. The method of claim 1, further comprising determining that a second emotional state of the viewer is unrelated to second content and related to second environmental characteristics by:
determining that the second emotional state of the viewer comprises the viewer being fearful;
determining that the second environmental characteristics indicate a tornado warning; and
determining that the viewer being fearful is based on the tornado warning.

16. An apparatus comprising:
one or more processors; and
memory storing instructions that, when executed by the one or more processors, cause the apparatus to:
receive a timestamp associated with a first media element displayed to a viewer and information indicating environmental characteristics of an environment associated with the viewer;
receive, at a time associated with the timestamp, information indicative of a change in one or more physical attributes of the viewer, wherein the one or more physical attributes comprise one or more of: a viewer position, a facial expression, or a sound output by the viewer;
determine, based on the timestamp, content of the first media element displayed to the viewer;
determine an emotional state, of the viewer, indicated by the change in the one or more physical attributes of the viewer;
determine, based on determining that the emotional state is related to the content and unrelated to the environmental characteristics, a current level of interest of the viewer in the content at the time; and
based on the current level of interest of the viewer in the content at the time and based on past reactions of the viewer to media elements and the content of the first media element, send a second media element to the viewer.

17. The apparatus of claim 16, wherein the instructions, when executed by the one or more processors, further cause the apparatus to:
receive, from a sensor device, information related to one or more sensor readings associated with the viewer.

18. The apparatus of claim 16, wherein the first media element and second media element are both portions of a same video content.

19. The apparatus of claim 16, wherein the second media element comprises information about the first media element.

20. The apparatus of claim 16, wherein the second media element comprises an offer to sell the first media element or an item displayed in the first media element to the viewer.

21. The apparatus of claim 16, wherein the instructions, when executed by the one or more processors, further cause the apparatus to:
offer to present the second media element to the viewer, and
send the second media element by sending the second media element to the viewer after the first media element is presented to the viewer.

22. A method comprising:
displaying a first media element to a viewer;
receiving a timestamp associated with the first media element and information indicating environmental characteristics of an environment associated with the viewer;
determining, by a computing device, one or more physical attributes of the viewer during display of the first media element, wherein the one or more physical attributes comprise one or more of: a viewer position, a facial expression, or a sound output by the viewer;
determining, based on the timestamp, content of the displayed first media element;
determining an emotional state, of the viewer, indicated by the one or more physical attributes of the viewer;
determining, based on determining that the emotional state is related to the content and unrelated to the environmental characteristics, a current level of interest of the viewer in the displayed first media element; and
based on the current level of interest of the viewer and based on past reactions of the viewer to media elements and the first media element, offering to present a second media element to the viewer.

23. The method of claim 22, wherein the second media element comprises information about the first media element.

24. The method of claim 22, further comprising selecting the second media element based at least in part on a location where the viewer is determined to be.

25. The method of claim 22, wherein the offering to present the second media element to the viewer comprises offering to record a streaming media that the viewer can request for replay at a later time.

* * * * *

UNITED STATES PATENT AND TRADEMARK OFFICE
CERTIFICATE OF CORRECTION

| | | |
|---|---|---|
| PATENT NO. | : 11,707,216 B2 | Page 1 of 1 |
| APPLICATION NO. | : 15/215677 | |
| DATED | : July 25, 2023 | |
| INVENTOR(S) | : Sarah Friant | |

It is certified that error appears in the above-identified patent and that said Letters Patent is hereby corrected as shown below:

On the Title Page

Page 2, item (56) OTHER PUBLICATIONS Column 2, Line 1:
Delete "Ratal," and insert --Rafal,--

In the Specification

Detailed Description, Column 4, Line 33:
Delete "rate" and insert --data--

Detailed Description, Column 4, Line 54:
Delete "129" and insert --131--

Detailed Description, Column 4, Line 54:
Delete "131." and insert --129.--

Detailed Description, Column 5, Line 45:
Delete "208." and insert --240.--

Detailed Description, Column 6, Line 24:
Delete "first" and insert --fist--

In the Claims

Claim 16, Column 18, Line 7:
After "and", delete "the content of"

Signed and Sealed this
Twenty-first Day of January, 2025

Coke Morgan Stewart
*Acting Director of the United States Patent and Trademark Office*